(12) United States Patent
Towler

(10) Patent No.: US 8,460,240 B2
(45) Date of Patent: Jun. 11, 2013

(54) INFLATABLE TOROIDAL-SHAPED BALLOONS

(75) Inventor: Jeffrey Towler, Wilmington, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 1165 days.

(21) Appl. No.: 11/501,148

(22) Filed: Aug. 7, 2006

(65) Prior Publication Data

US 2008/0086083 A1   Apr. 10, 2008

(51) Int. Cl.
*A61M 29/00* (2006.01)
*A61M 37/00* (2006.01)
*A61M 31/00* (2006.01)

(52) U.S. Cl.
USPC ............. 604/103.07; 604/96.01; 604/509

(58) Field of Classification Search
USPC .......... 604/96.01, 97.01, 101.01, 101.02, 604/103, 103.05, 103.07, 103.08, 103.09
See application file for complete search history.

(56) References Cited

U.S. PATENT DOCUMENTS

| | | |
|---|---|---|
| 1,690,995 A | 11/1928 | Pratt |
| 3,640,282 A | 2/1972 | Kamen |
| 3,746,003 A | 7/1973 | Blake et al. |
| 3,953,566 A | 4/1976 | Gore ............. 264/288 |
| 4,003,382 A | 1/1977 | Dyke |
| 4,106,509 A | 8/1978 | McWhorter |
| 4,187,390 A | 2/1980 | Gore |
| 4,194,041 A | 3/1980 | Gore et al. |
| 4,279,245 A | 7/1981 | Takagi et al. |
| 4,280,500 A | 7/1981 | Ono |
| 4,304,010 A | 12/1981 | Mano |
| 4,327,736 A | 5/1982 | Inoue |
| 4,338,942 A | 7/1982 | Fogarty |
| 4,403,612 A | 9/1983 | Fogarty |
| 4,443,511 A | 4/1984 | Worden et al. |
| 4,490,421 A | 12/1984 | Levy |
| 4,573,966 A | 3/1986 | Weikl et al. |
| 4,596,839 A | 6/1986 | Peters |
| 4,608,984 A | 9/1986 | Fogarty |
| 4,613,544 A | 9/1986 | Burleigh |
| 4,619,641 A | 10/1986 | Schanzer |
| 4,637,396 A | 1/1987 | Cook |
| 4,650,466 A | 3/1987 | Luther |
| 4,702,252 A | 10/1987 | Brooks et al. |
| 4,706,670 A | 11/1987 | Andersen et al. ............. 128/344 |
| 4,713,070 A | 12/1987 | Mano |
| 4,737,219 A | 4/1988 | Taller et al. |

(Continued)

FOREIGN PATENT DOCUMENTS

| | | |
|---|---|---|
| EP | 0 372 088 | 6/1990 |
| EP | 372088 | 6/1990 |

(Continued)

OTHER PUBLICATIONS

Dillon M E, Silicone and Poly (tetrafluuoroethylene) Interpenetrating Polymer Networks, 1994 American Chemical Society.

*Primary Examiner* — Kevin C Sirmons
*Assistant Examiner* — Andrew Gilbert
(74) *Attorney, Agent, or Firm* — Kristine Waddell

(57) ABSTRACT

An inflatable toroidal-shaped balloon for medical use is provided with a central opening traversing the balloon in an inflated state. The balloon is useful to achieve larger outer diameters than conventional balloons.

50 Claims, 16 Drawing Sheets

U.S. PATENT DOCUMENTS

| | | | |
|---|---|---|---|
| 4,739,762 A | 4/1988 | Palmaz | |
| 4,743,480 A | 5/1988 | Campbell et al. | |
| 4,764,560 A | 8/1988 | Mitchell | |
| 4,816,339 A | 3/1989 | Tu et al. | |
| 4,819,751 A | 4/1989 | Shimada et al. | |
| 4,832,688 A | 5/1989 | Sagae et al. | |
| 4,896,669 A | 1/1990 | Bhate et al. | |
| 4,946,464 A | 8/1990 | Pevsner | |
| 4,955,899 A | 9/1990 | Dell Coma et al. | |
| 5,041,047 A | 8/1991 | Casale | |
| 5,061,276 A | 10/1991 | Tu et al. | |
| 5,066,298 A | 11/1991 | Hess | |
| 5,071,609 A | 12/1991 | Tu et al. | |
| 5,087,244 A | 2/1992 | Wolinsky et al. | |
| 5,100,429 A | 3/1992 | Sinofsky et al. | |
| 5,108,370 A * | 4/1992 | Walinsky | 604/102.02 |
| 5,112,304 A | 5/1992 | Barlow et al. | |
| 5,116,318 A | 5/1992 | Hillstead | |
| 5,137,512 A | 8/1992 | Burns et al. | |
| 5,147,302 A | 9/1992 | Euteneuer et al. | |
| 5,152,782 A | 10/1992 | Kowligi et al. | |
| 5,171,297 A | 12/1992 | Barlow et al. | |
| 5,192,296 A | 3/1993 | Bhate et al. | |
| 5,195,970 A | 3/1993 | Gahara | |
| 5,197,978 A | 3/1993 | Hess | |
| 5,201,706 A | 4/1993 | Noguchi et al. | |
| 5,211,654 A | 5/1993 | Kaltenbach | |
| 5,213,576 A | 5/1993 | Abiuso et al. | |
| 5,226,880 A | 7/1993 | Martin | |
| 5,236,659 A | 8/1993 | Pinchuk et al. | |
| 5,254,090 A | 10/1993 | Lombardi et al. | |
| 5,256,143 A | 10/1993 | Miller et al. | |
| 5,286,254 A | 2/1994 | Shapland et al. | |
| 5,290,306 A | 3/1994 | Trotta et al. | |
| 5,304,120 A | 4/1994 | Crandell et al. | |
| 5,304,214 A | 4/1994 | DeFord et al. | |
| 5,304,340 A | 4/1994 | Downey | |
| 5,308,356 A | 5/1994 | Blackshear | |
| 5,330,429 A | 7/1994 | Noguchi et al. | |
| 5,338,299 A | 8/1994 | Barlow | |
| 5,342,305 A | 8/1994 | Shonk | |
| 5,342,348 A | 8/1994 | Kaplan | |
| 5,348,538 A | 9/1994 | Wang et al. | |
| 5,358,486 A | 10/1994 | Saab | |
| 5,358,516 A | 10/1994 | Myers et al. | |
| 5,366,442 A | 11/1994 | Wang et al. | |
| 5,366,472 A | 11/1994 | Hillstead | |
| 5,370,618 A | 12/1994 | Leonhardt | |
| 5,403,340 A | 4/1995 | Wang et al. | |
| 5,409,495 A | 4/1995 | Osborn | |
| 5,415,636 A | 5/1995 | Forman | |
| 5,425,710 A | 6/1995 | Khair et al. | |
| 5,429,605 A | 7/1995 | Richling | |
| 5,456,661 A | 10/1995 | Narciso | |
| 5,458,568 A | 10/1995 | Racchini et al. | |
| 5,458,605 A | 10/1995 | Klemm | |
| 5,466,252 A | 11/1995 | Soukup et al. | |
| 5,470,313 A | 11/1995 | Crocker et al. | |
| 5,470,314 A * | 11/1995 | Walinsky | 604/103.11 |
| 5,476,489 A | 12/1995 | Bacino | 210/500.36 |
| 5,478,320 A | 12/1995 | Trotta | |
| 5,478,349 A | 12/1995 | Nicholas | |
| 5,484,411 A | 1/1996 | Inderbitzen et al. | |
| 5,490,839 A | 2/1996 | Wang et al. | |
| 5,496,276 A | 3/1996 | Wang et al. | |
| 5,498,238 A | 3/1996 | Shapland et al. | |
| 5,499,973 A | 3/1996 | Saab | |
| 5,499,980 A | 3/1996 | Euteneuer | |
| 5,499,995 A | 3/1996 | Teirstein | |
| 5,500,180 A | 3/1996 | Anderson et al. | |
| 5,500,181 A | 3/1996 | Wang et al. | |
| 5,512,051 A | 4/1996 | Wang et al. | |
| 5,519,172 A | 5/1996 | Spencer et al. | |
| 5,527,282 A | 6/1996 | Segal | |
| 5,529,820 A | 6/1996 | Nomi et al. | |
| 5,571,089 A | 11/1996 | Crocker | |
| 5,609,605 A | 3/1997 | Marshall et al. | |
| 5,613,979 A | 3/1997 | Trotta et al. | |
| 5,620,649 A | 4/1997 | Trotta | |
| 5,641,373 A | 6/1997 | Shannon et al. | |
| 5,645,560 A | 7/1997 | Crocker et al. | |
| 5,647,848 A | 7/1997 | Jorgensen | 604/96 |
| 5,716,340 A * | 2/1998 | Schweich et al. | 604/101.05 |
| 5,716,396 A | 2/1998 | Williams, Jr. | |
| 5,752,934 A * | 5/1998 | Campbell et al. | 604/96.01 |
| 5,766,201 A | 6/1998 | Ravenscroft et al. | |
| 5,797,877 A | 8/1998 | Hamilton et al. | |
| 5,807,327 A | 9/1998 | Green et al. | |
| 5,843,116 A | 12/1998 | Crocker et al. | |
| 5,868,704 A | 2/1999 | Campbell et al. | |
| 5,868,708 A | 2/1999 | Hart et al. | |
| 5,893,840 A | 4/1999 | Hull et al. | |
| 5,908,406 A | 6/1999 | Ostapchenko et al. | |
| 5,944,734 A | 8/1999 | Hermann et al. | |
| 5,951,941 A | 9/1999 | Wang et al. | |
| 5,954,745 A * | 9/1999 | Gertler et al. | 606/200 |
| 5,972,441 A * | 10/1999 | Campbell et al. | 428/34.1 |
| 6,010,480 A | 1/2000 | Abele et al. | |
| 6,013,092 A | 1/2000 | Dehdashtian | |
| 6,027,779 A | 2/2000 | Campbell et al. | |
| 6,048,356 A * | 4/2000 | Ravenscroft et al. | 606/194 |
| 6,120,477 A | 9/2000 | Campbell et al. | |
| 6,132,824 A | 10/2000 | Hamlin | |
| 6,234,995 B1 | 5/2001 | Peacock, III | |
| 6,287,290 B1 | 9/2001 | Perkins et al. | |
| 6,287,314 B1 | 9/2001 | Lee et al. | |
| 6,319,249 B1 | 11/2001 | Tollner | |
| 6,319,259 B1 | 11/2001 | Lee et al. | |
| 6,319,529 B1 | 11/2001 | Thompson | |
| 6,336,937 B1 * | 1/2002 | Vonesh et al. | 623/1.13 |
| 6,375,637 B1 | 4/2002 | Campbell et al. | |
| 6,428,506 B1 | 8/2002 | Simhambhatla et al. | |
| 6,482,348 B1 | 11/2002 | Wang et al. | |
| 6,488,688 B2 | 12/2002 | Lim et al. | |
| 6,572,813 B1 | 6/2003 | Zhang et al. | |
| 6,602,224 B1 | 8/2003 | Simhambhatla | |
| 6,663,646 B1 | 12/2003 | Shah | |
| 6,746,425 B1 | 6/2004 | Beckham | |
| 6,756,094 B1 | 6/2004 | Wang et al. | |
| 6,887,227 B1 * | 5/2005 | Barbut | 604/500 |
| 6,890,395 B2 | 5/2005 | Simhambhatla | |
| 6,905,743 B1 | 6/2005 | Chen et al. | |
| 6,923,827 B2 * | 8/2005 | Campbell et al. | 623/1.11 |
| 6,939,593 B2 | 9/2005 | Wang | |
| 6,977,103 B2 | 12/2005 | Chen et al. | |
| 7,052,507 B2 | 5/2006 | Wakuda et al. | |
| 7,195,638 B1 * | 3/2007 | Sridharan | 606/194 |
| 7,279,208 B1 | 10/2007 | Goffena et al. | |
| 7,306,729 B2 * | 12/2007 | Bacino et al. | 210/500.22 |
| 7,625,337 B2 * | 12/2009 | Campbell et al. | 600/156 |
| 7,785,290 B2 * | 8/2010 | Alpini et al. | 604/103.06 |
| 2001/0008970 A1 | 7/2001 | Ravenscroft et al. | |
| 2002/0087165 A1 | 7/2002 | Lee et al. | |
| 2002/0163104 A1 | 11/2002 | Motsenbocker | |
| 2003/0074016 A1 * | 4/2003 | Campbell et al. | 606/192 |
| 2003/0083687 A1 | 5/2003 | Paliazza | |
| 2003/0088209 A1 | 5/2003 | Chiu et al. | |
| 2003/0130716 A1 | 7/2003 | Weber | |
| 2003/0211258 A1 * | 11/2003 | Sridharan et al. | 428/35.2 |
| 2004/0015183 A1 | 1/2004 | Lim et al. | |
| 2004/0082965 A1 * | 4/2004 | Beckham | 606/192 |
| 2004/0191442 A1 | 9/2004 | Lim | |
| 2004/0199202 A1 * | 10/2004 | Dubrul et al. | 606/200 |
| 2004/0254625 A1 | 12/2004 | Stephens et al. | |
| 2005/0015048 A1 * | 1/2005 | Chiu et al. | 604/101.04 |
| 2005/0038503 A1 | 2/2005 | Greenhalgh et al. | |
| 2005/0267409 A1 | 12/2005 | Shkolnik | |
| 2005/0273152 A1 | 12/2005 | Campbell et al. | |
| 2006/0085024 A1 | 4/2006 | Pepper et al. | |
| 2006/0136032 A1 * | 6/2006 | Legarda et al. | 623/1.11 |
| 2006/0161102 A1 | 7/2006 | Newcomb et al. | |
| 2006/0271091 A1 | 11/2006 | Campbell et al. | |
| 2007/0055301 A1 | 3/2007 | Campbell et al. | |
| 2007/0061000 A1 | 3/2007 | Campbell et al. | |
| 2007/0219489 A1 | 9/2007 | Johnson et al. | |
| 2008/0125711 A1 | 5/2008 | Alpini et al. | |
| 2008/0140173 A1 | 6/2008 | Eskaros et al. | |

| | | | |
|---|---|---|---|
| 2008/0255507 A1 | 10/2008 | Mushtaha | |
| 2008/0257155 A1 | 10/2008 | Bacino et al. | |
| 2008/0312730 A1 | 12/2008 | Campbell et al. | |
| 2009/0032470 A1 | 2/2009 | Bacino et al. | |
| 2009/0053103 A1 | 2/2009 | Mortimer et al. | |
| 2009/0283206 A1 | 11/2009 | Eskaros et al. | |
| 2010/0049123 A1 | 2/2010 | Alpini et al. | |
| 2010/0262178 A1 | 10/2010 | Alpini et al. | |

FOREIGN PATENT DOCUMENTS

| | | |
|---|---|---|
| EP | 0 540 858 | 5/1993 |
| EP | 0 628 586 | 12/1994 |
| EP | 0 628586 | 12/1994 |
| EP | 737488 | 10/1996 |
| EP | 769307 | 4/1997 |
| EP | 0 829 269 | 3/1998 |
| GB | 1566674 | 5/1980 |
| NL | 1008178 | 8/1999 |
| WO | 90/14054 | 11/1990 |
| WO | 94/02185 | 2/1994 |
| WO | 95/05555 | 2/1995 |
| WO | 95/09667 | 4/1995 |
| WO | 95/17920 | 7/1995 |
| WO | 96/14895 | 5/1996 |
| WO | 96/40350 | 12/1996 |
| WO | 97/02791 | 1/1997 |
| WO | 97/40877 | 11/1997 |
| WO | 02/068011 | 9/2002 |
| WO | 03/000307 | 1/2003 |
| WO | 2008/021002 | 2/2008 |
| WO | 2008/021003 | 2/2008 |
| WO | 2008/021006 | 2/2008 |
| WO | 2008/021013 | 2/2008 |

* cited by examiner

INFLATABLE TOROIDAL-SHAPED BALLOONS

BACKGROUND OF THE INVENTION

The present invention relates to inflatable balloons and more particularly to inflatable toroidal-shaped balloon catheters for medical procedures.

Balloon catheters are well known in the art. Such catheters are employed in a variety of medical procedures, including dilation of narrowed blood vessels, placement of stents and other implants, and temporary occlusion of blood vessels, and other vascular uses.

In a typical application, the balloon is advanced to the desired location in the vascular system. The balloon is then pressure-expanded in accordance with a medical procedure. Thereafter, the pressure is removed from the balloon, allowing the balloon to contract and permit removal of the catheter. It is to be appreciated that the balloon is preferably formed of an elastomeric material which is readily pressure-expanded, yet will also readily contract upon removal of the inflation pressure.

Procedures such as these are generally considered minimally invasive, and are often performed in a manner which minimizes disruption to the patient's body. As a result, catheters are often inserted from a location remote from the region to be treated. For example, during angioplasty procedures involving coronary vessels, the balloon catheter is typically inserted into the femoral artery in the groin region of the patient, and then advanced through such vessel into the coronary region of the patient. These catheters typically include some type of radiopaque marker to allow the physician performing the procedure to monitor the progress of the catheter through the body. However, because the balloon portion of the catheter is not visible to the physician, the balloon may be over inflated without the physician's awareness. This is particularly concerning when large diameter balloons are employed in medical procedures because the maximum hoop stress of the inflated balloon material can more easily be exceeded causing the balloon to rupture or burst.

There are two main forms of balloon catheter devices, compliant and non-compliant balloons. Non-compliant balloons employ a relatively strong but generally inelastic material (e.g., polyester) folded into a compact, small diameter cross section. These relatively stiff catheters are used to compact hard deposits in vessels. Due to the need for strength and stiffness, these devices are rated to employ high inflation pressures, usually up to about 8 to 12 atmospheres depending on rated diameter. They tend to be self-limiting as to diameter, thus they will normally distend up to the rated diameter and not distend appreciably beyond this diameter until rupture due to over-pressurization. While the inelastic material of the balloon is generally effective in compacting deposits, it tends to collapse unevenly upon deflation, leaving a flattened, folded balloon substantially larger in cross section than the balloon was prior to inflation. This enlarged, folded balloon may be difficult to remove, especially from small vessels. By contrast, compliant balloons are used to remove soft deposits, such as thrombus, where a soft and tacky material such as a latex provides an effective extraction means. Latex and other highly elastic materials generally will expand continuously upon increased internal pressure until the material bursts. As a result, these catheters are generally rated by volume (e.g., 0.3 cc) in order to properly distend to a desired size. Although relatively weak, these catheters do have the advantage that they tend to readily return to their initial size and dimensions following inflation and subsequent deflation. The weak nature of the elastomer material used in these types of balloon catheters has restricted their use to small diameter balloon applications; typically less than 4 to 5 mm diameter. The stress generated in the inflatable balloon material is defined as hoop stress and is a function of the product of the inflation pressure and the inner diameter of the inflated balloon, divided by the wall thickness of the inflated balloon. Accordingly, the hoop stress increases linearly with increasing balloon diameter. Therefore, there have been efforts to reinforce embolectomy elastic balloon catheters.

Some of the catheter balloons constructed of both elastomeric and non-elastomeric materials have been described previously. As the length of their balloon portion decreases, the length of the movable portion of the outer tubing increases and by proper selection of internal diameters and lengths of the two portions, the shortening of the balloon is offset.

U.S. Pat. No. 5,647,848 teaches a structure formed of helically extending fibers, including bundles of continuous monofilaments, aramide, polyethylene, steel, polyester, glass, carbon, and ceramics. The fibers are positioned in an elastomer such that the fibers lie at an angle which is less than a neutral angle of 54.73 degrees relative to the axis of the balloon when the balloon is unpressurized. With the utilization of rigid fibers the balloon will be non-compliant in its fully inflated state.

Some medical procedures which require the use of a relatively large diameter balloon would greatly benefit from a balloon with a small uniflated diameter that would return to that initial size and dimensions following inflation and subsequent deflation. The means for reinforcing the elastic balloon catheters to date have not addressed both the low profile and high burst pressure requirements for large diameter balloon applications. Accordingly, there is a need in the art for large diameter elastomeric balloons that can maintain a shape profile upon inflation and that can withstand high inflation pressure. In addition, there is a need in the art for a large diameter elastomeric balloon with a relatively short axial length, and a toroidal-shaped inflated balloon that maintains a shape profile upon inflation, can withstand high inflation pressure, and can be made to only partially occlude the vessel upon inflation.

Temporary brachytherapy is a medical application that involves positioning catheters into areas such as the prostate or colon, for the purpose of giving a series of radiation treatments through these catheters. The catheters are easily pulled out after the treatment and no radioactive material is left in the body. A balloon catheter that secures the radioactive material in the center of a vessel would be advantageous in these applications as it would provide for more uniform dosing or treatment of the vessel, tube or orifice with radiation and minimize any excessive dosing to the interior wall of the vessel. There is a need for a balloon catheter that can secure the radioactive element and reach large diameters for applications such as colon temporary brachytherapy.

The use of bioresorbable materials in balloon catheters have been used to seal wounds and to repair vessels. In such applications, a toroidal-shaped bioresorbable balloon would be ideal for sealing the wound in a minimally invasive manner. In addition, a toroidal-shaped balloon can be used in large-neck aneurysms to bridge over the large neck and make a small neck aneurysm, which is then easier to pack in Guglielmi Detachable Coils. Intestinal wall reinforcement is another application for a toroidal-shaped bioresorbable balloon.

SUMMARY OF THE INVENTION

The present invention is a toroidal-shaped balloon catheter for use in a variety of surgical procedures. The toroidal-shaped balloons of the present invention can be made to reach large outer diameters and sustain high inflation pressures while maintaining their shape and can return to their pre-inflation shape upon deflation. In addition, the toroidal-shaped balloons of the present invention can be made to provide perfusion flow through the center or open region of the inflated balloon. Furthermore, the toroidal-shaped balloon of the present invention can be attached to a catheter for the purpose of delivering a device or treatment element such as a radioactive element through the center portion of the inflated balloon, or two balloons can be used to center a device or treatment element in the center of a vessel, tube or orifice.

The toroidal-shaped balloons of the present invention are anticipated to be particularly useful for various medical and surgical procedures, including angioplasty, stent or graft delivery and distention, and temporary brachytherapy as well as intestinal procedures.

DETAILED DESCRIPTION OF THE INVENTION

The present invention provides a toroidal-shaped balloon catheter for use in a variety of surgical procedures. The toroidal-shaped balloon of the present invention comprises a plurality of wrapped composite film layers formed into an elastomeric hollow body that is configured into a toroidal-shaped balloon and fixed in that shape. The balloon may be attached to the catheter is comprised of at least two passes of a composite balloon material.

Figure 1:
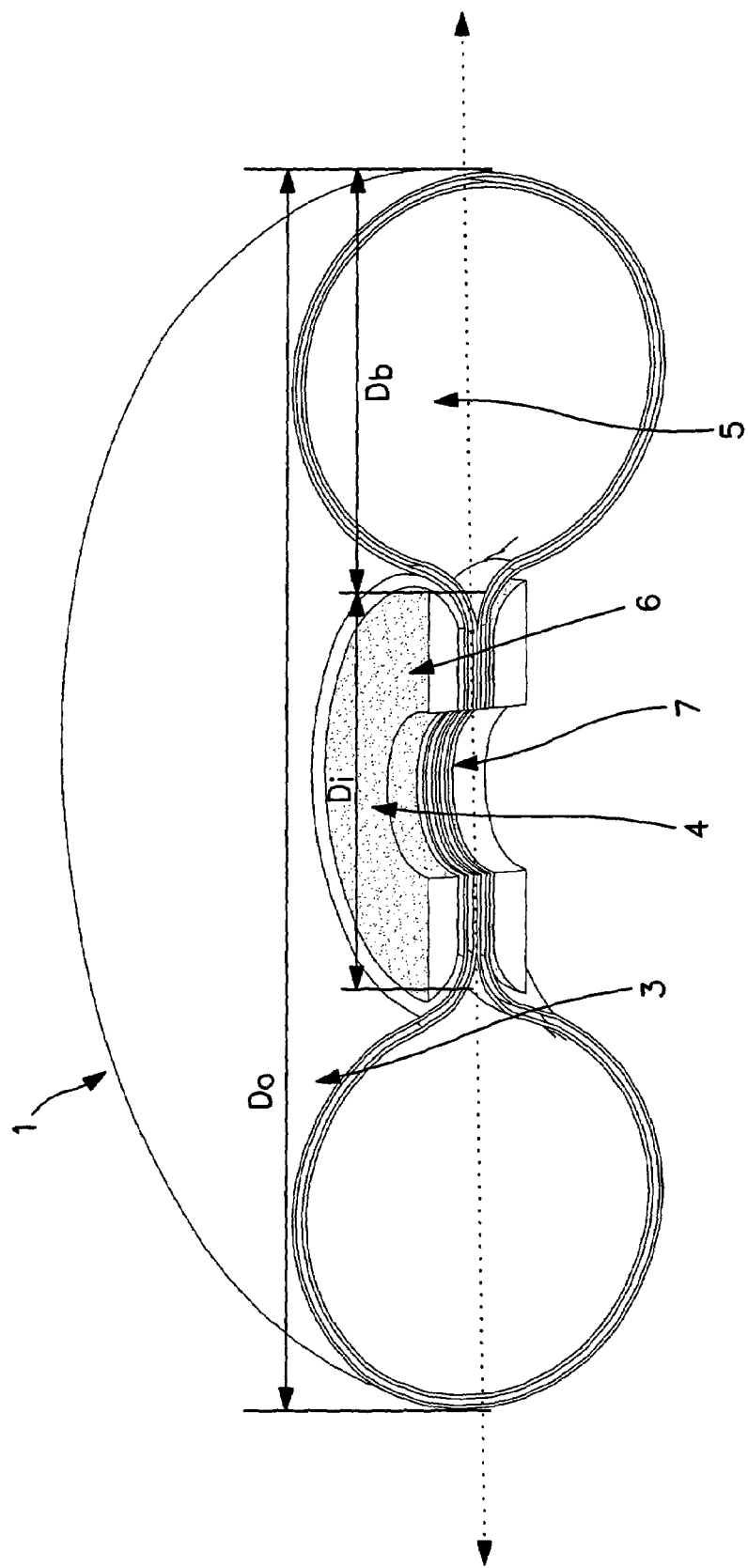
FIG. 1 shows a schematic representation of an inflated toroidal-shaped balloon cross-section.
Figure 2:
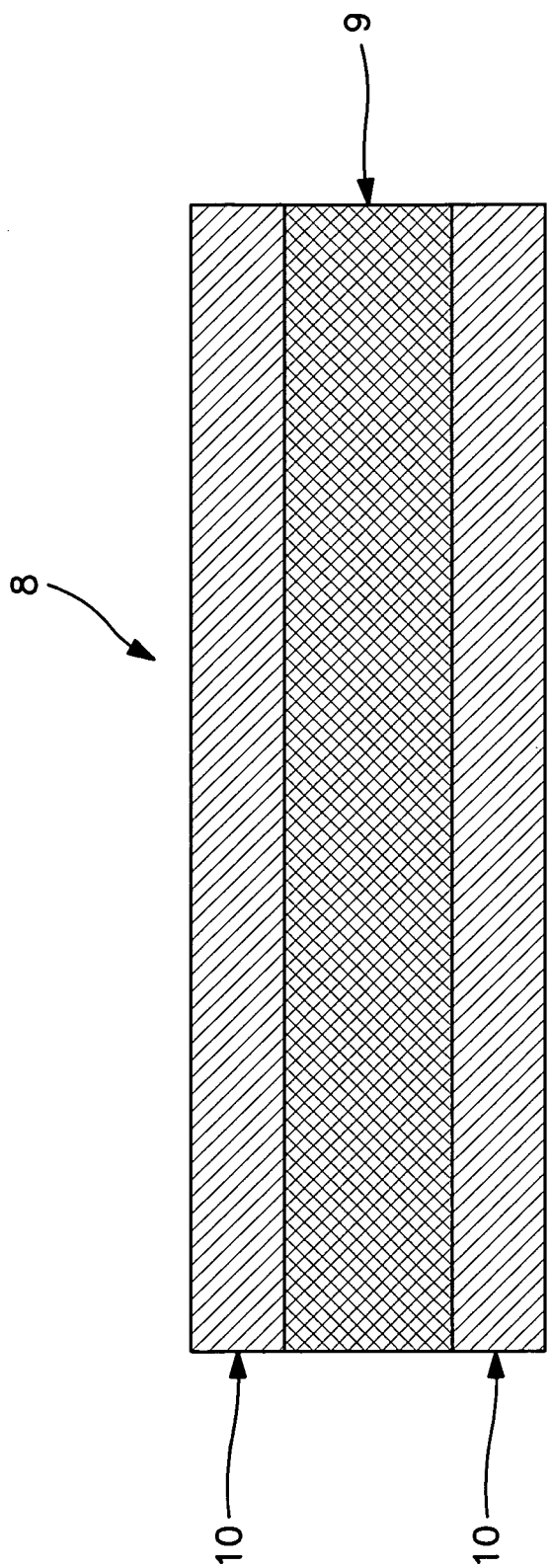
FIG. 2 shows a cross-section of a composite film with two polymer coating layers on the porous reinforcing polymer.
Figure 3:
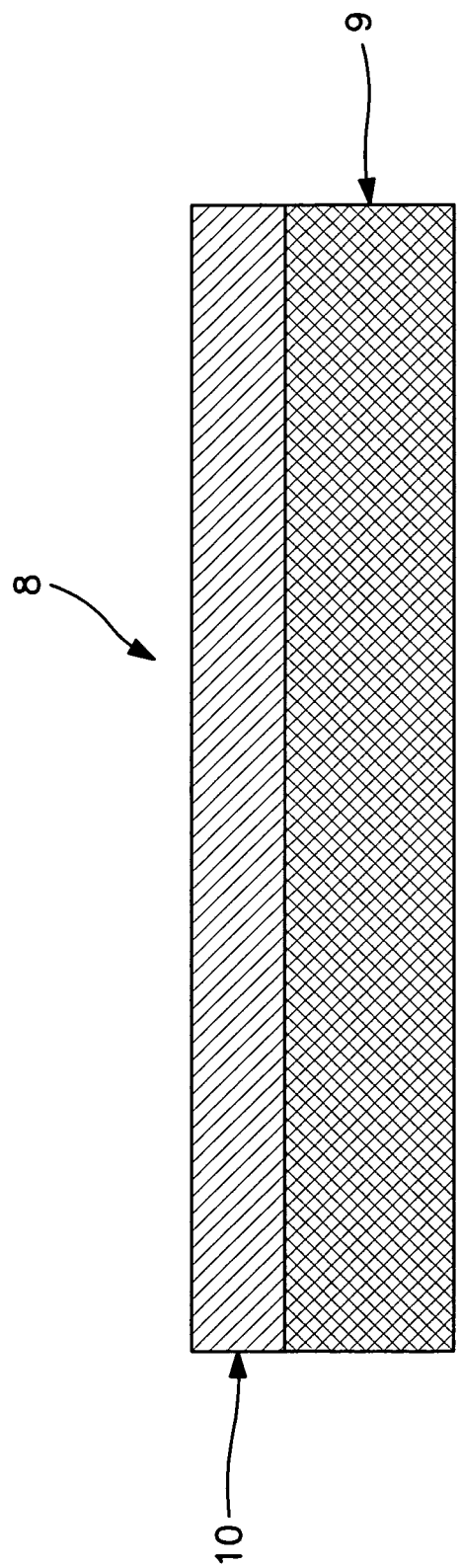
FIG. 3 shows a cross-section of a composite film with one polymer coating layer on the porous reinforcing polymer.
Figure 4:
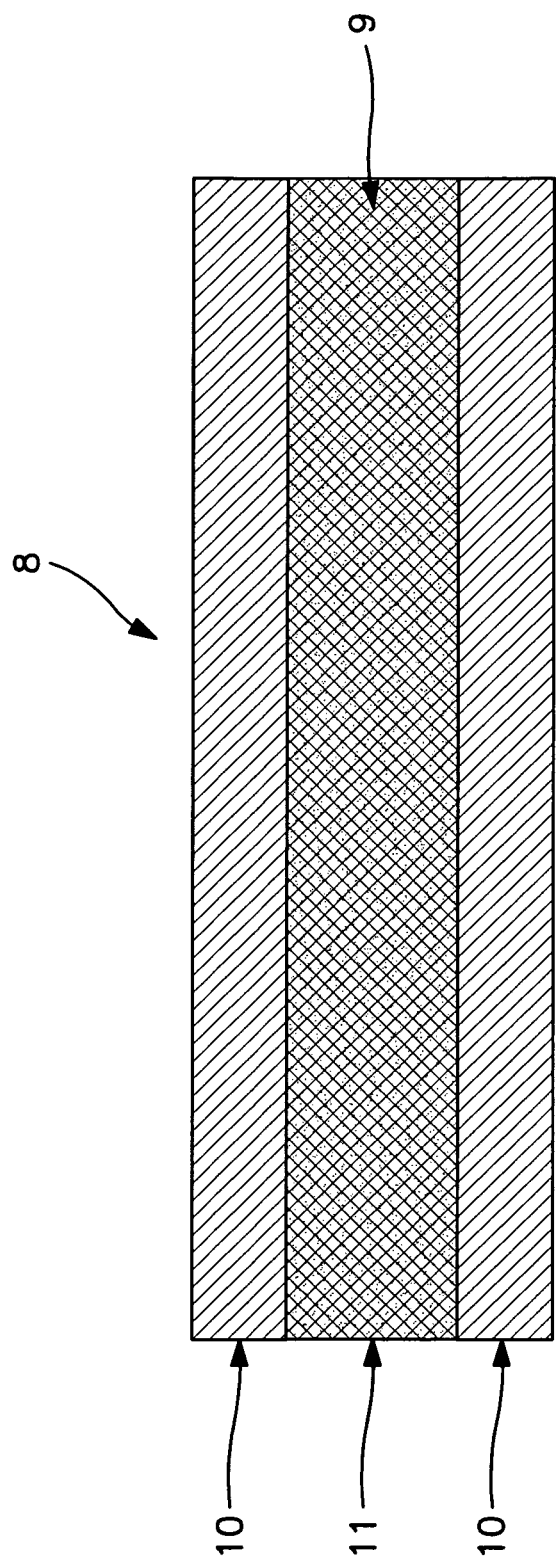
FIG. 4 shows a cross-section of a composite film with two polymer coating layers and polymer imbibed throughout the porous reinforcing.

The inflated toroidal-shaped balloon 1, as depicted in FIG. 1, can be made to have a much larger outer diameter 3 than what would normally be achievable with an angioplasty type balloon configured in a traditional tube. The inflated toroidal-shaped balloon 1 also withstands high inflation pressure at larger outer diameter 3 measurements than traditionally possible, because the inflated balloon diameter 5 is much less than the outer diameter 3. The outer diameter 3 is defined as the distance measured by a length of a line running through the center of the balloon and spanning the distance between the outermost walls of the inflated shaped balloon. In addition, the inflated toroidal-shaped balloon 1 can withstand high inflation pressures at a large outer diameter 3 because the balloon is made out of a composite film, as shown in FIGS. 2 to 4, that incorporates a porous reinforcing polymer 9. The composite film 8 is applied in wrapped layers 2 to form a desired shape, and sealed region 6, depending upon desired application. In addition, another advantage is that perfusive flow can be achieved through the open region 7 of the toroidal-shaped balloon 1.

Figure 5:
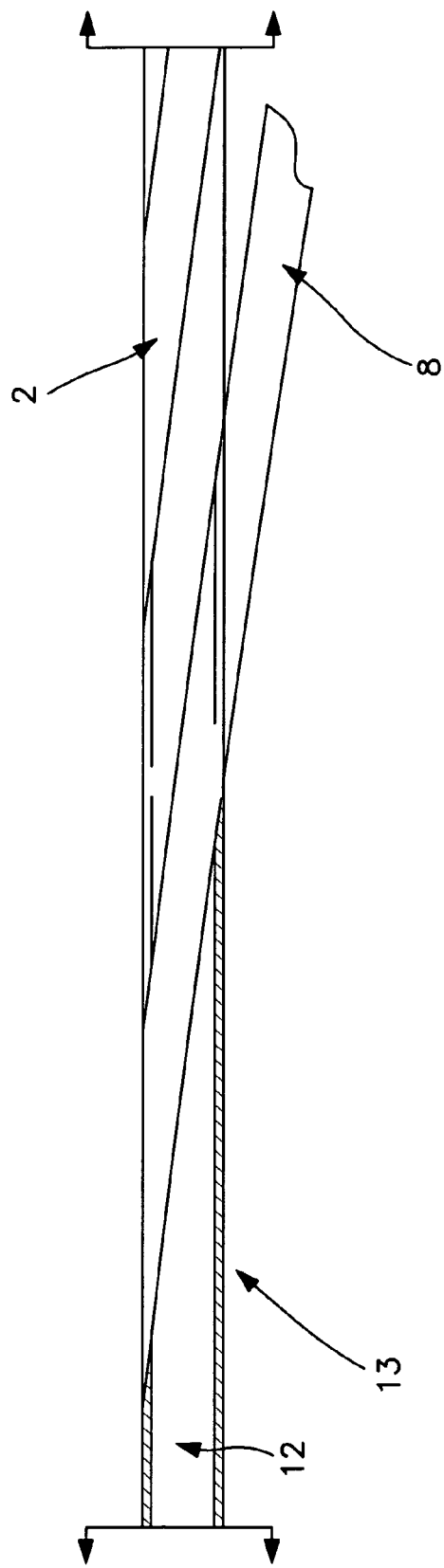
FIG. 5 shows a schematic representation of the composite film helically wrapped around a tube.
Figure 6:
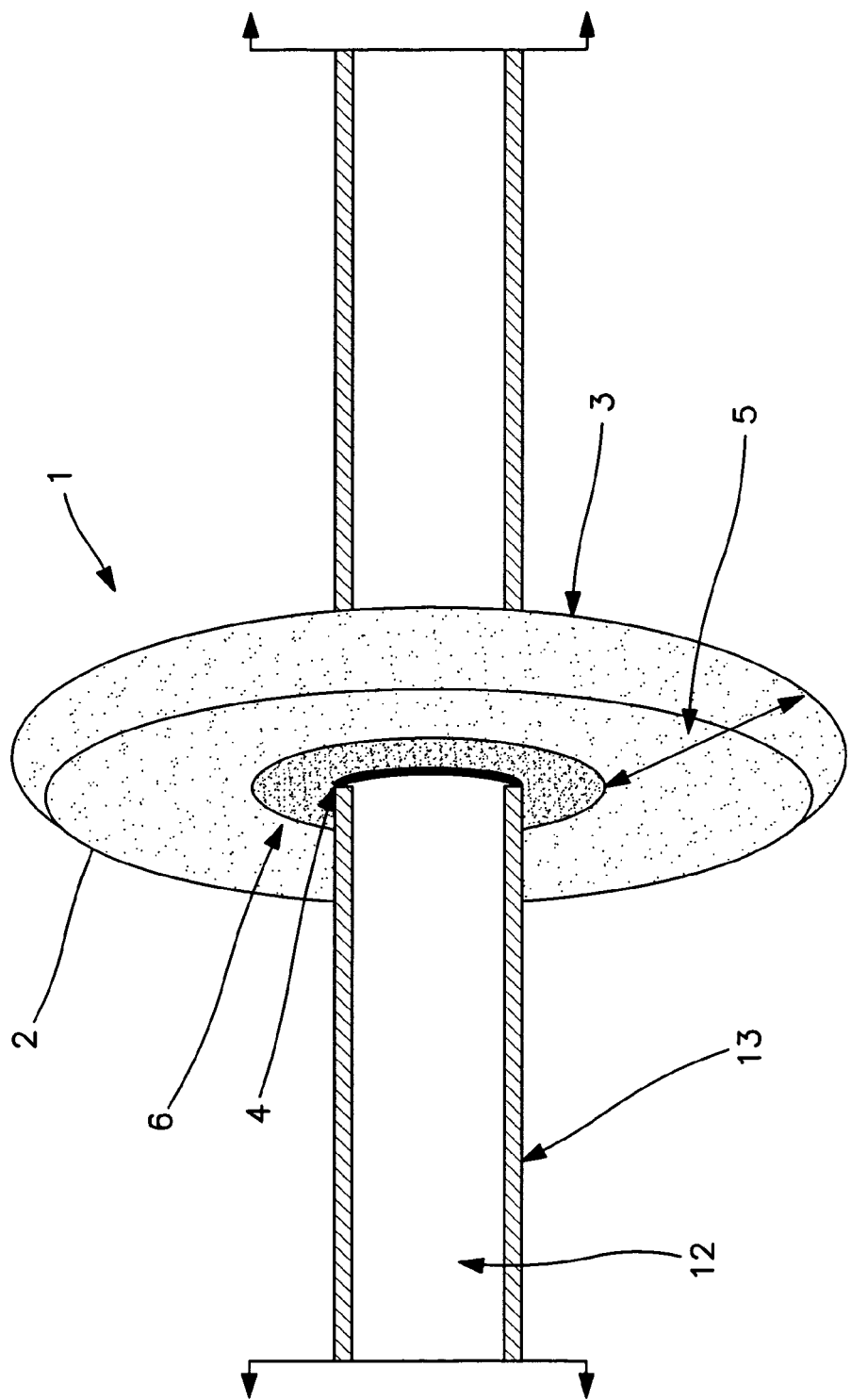
FIG. 6 shows a schematic representation of an inflated toroidal-shaped balloon on a tube.

The toroidal-shaped balloon of the present invention comprises a plurality of wrapped layers 2 of balloon material. The balloon material is comprised of a composite film 8, such as shown in FIG. 5. An individual pass is comprised of one or more layers of material which are laid at a similar angle in relation to one another. A layer is considered to be one thickness of balloon material which may be wrapped, folded, laid or weaved over, around, beside or under another thickness. A longitudinal pass comprises a distinctive layer or series of layers of material which are wound to form a region or area distinct from surrounding or adjoining parts. For instance a pass may comprise multiple layers of balloon material wrapped at a 90 degree angle relative to the longitudinal axis. This exemplary pass may then be flanked by layers of balloon material wrapped at dissimilar angles in relation to the longitudinal axis, thus defining the boundary of the pass.

Figure 7:
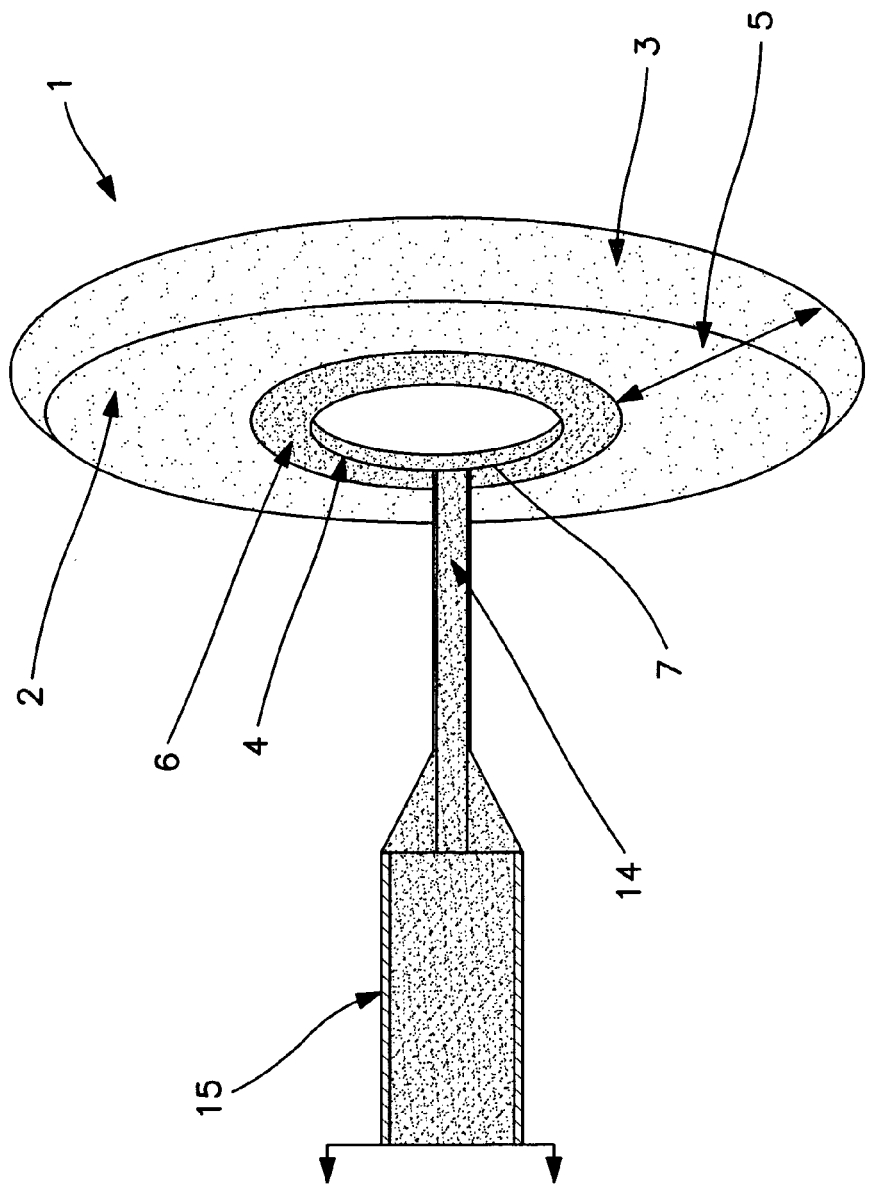
FIG. 7 shows a schematic representation of an inflated toroidal-shaped balloon catheter.
Figure 11:
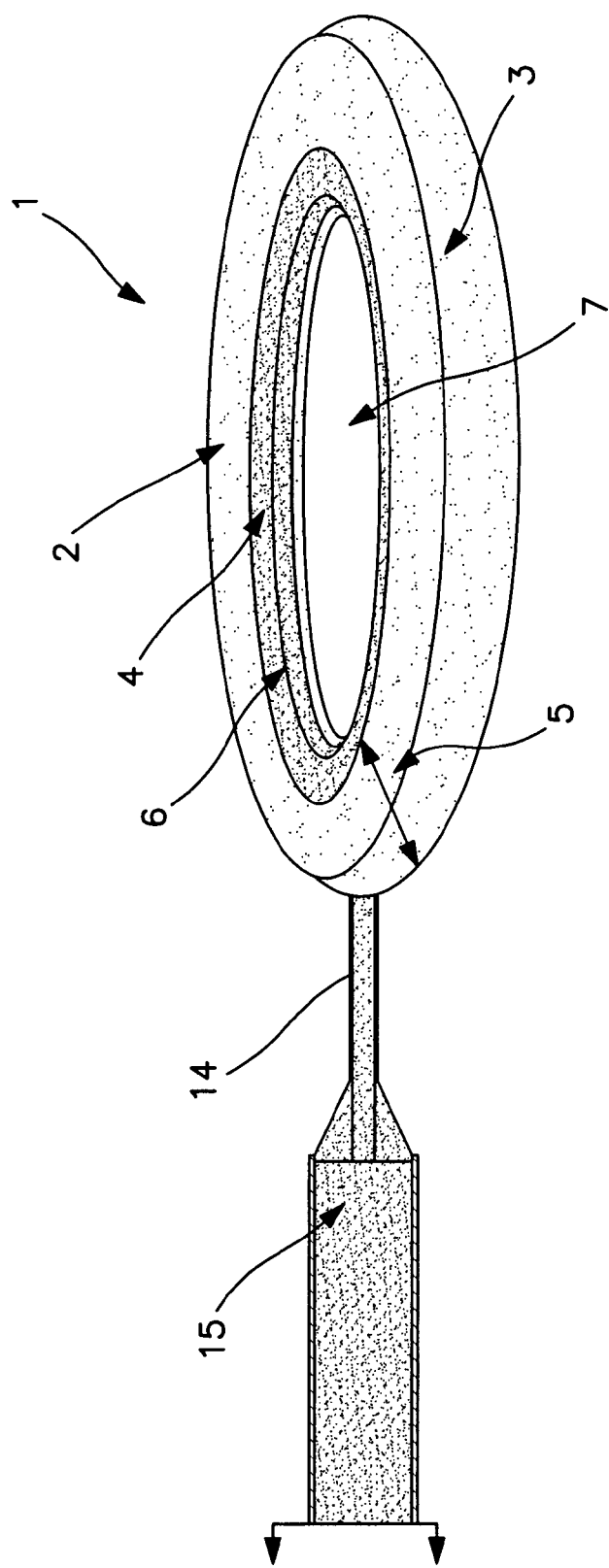
FIG. 11 shows a schematic representation of an inflated toroidal-shaped balloon catheter with an inflation tube connected along the outer diameter of the inflated balloon.
Figure 14:
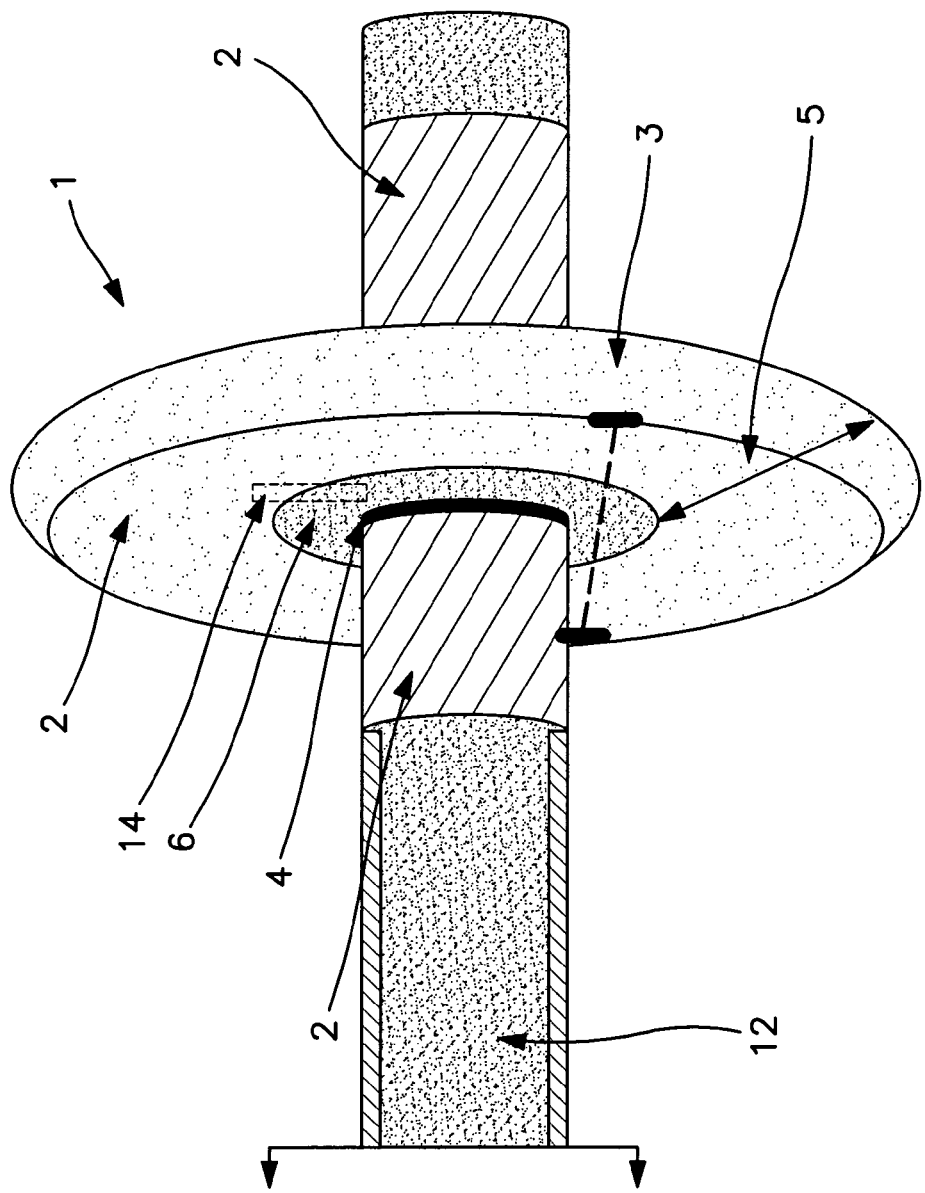
FIG. 14 shows a schematic representation of an inflated toroidal-shaped balloon catheter with an inflation tube located in the center of the balloon and additional length of unsealed wrapped layers sealed to the catheter.
Figure 15:
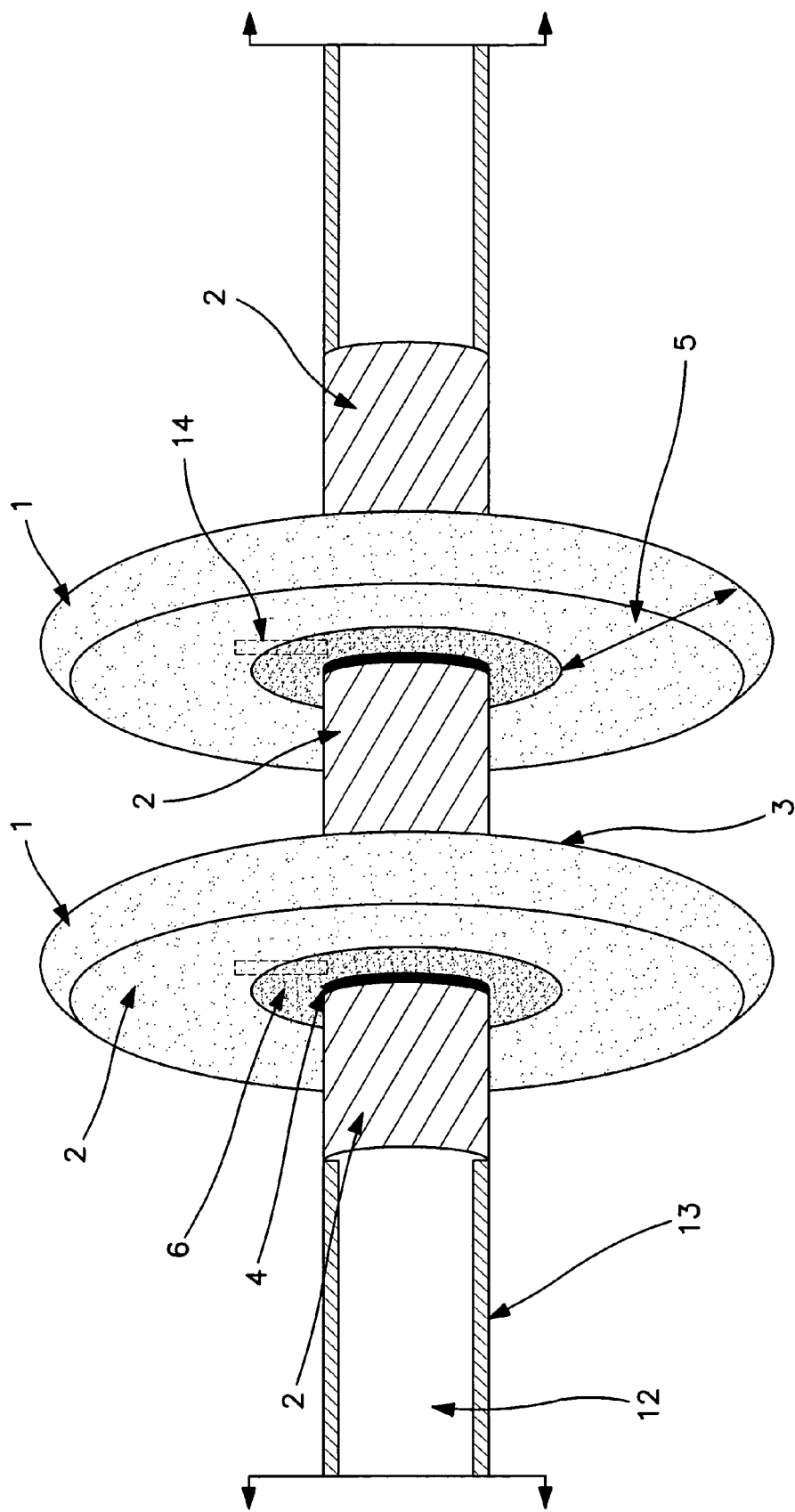
FIG. 15 shows a schematic representation of two inflated toroidal-shaped balloons with inflation tubes located in the center of each balloon and additional length of unsealed wrapped layers connecting the two balloons.

A pass of balloon material may be oriented helically, radially or longitudinally. By layers of balloon material it is meant to include pieces, threads, layers, filaments, membranes, or sheets of suitable balloon material. In helically oriented layers, the material is oriented so to form a balanced force angle in relation to each other upon inflation. The layers may further be wound upon themselves in subsequent passes. The composite film 8 is wrapped around a tube 12 that has a slip layer 13 or a easy release material on the outside surface of the tube 12. A tube made out of a low surface energy material such as PTFE or Perfluoralkoxy (PFA) would eliminate the need for a slip layer 13. The composite film 8 is preferably helically wrapped around the tube 12 at an angle of less than 55 degrees from the longitudinal axis of the tube. The layers are wrapped in opposing directions over top of each other. After the tube has been wrapped with the composite film 8, the wrapped layers 2 are heated to bond the wrapped layers together. Any means can be used to bond the wrapped layers together, such as heat, ultrasonic welding, or adhesives. After the wrapped layers are bonded, they are then gently inflated through a hole in the tube 12 and pinched together and sealed to form a sealed region 6. Heat or ultrasonic welding or adhesive can be employed to create the sealed region 6. The inner diameter 4 of the toroidal-shaped balloon as depicted in FIG. 1, is defined by the length of a line running through the center of the balloon and spanning the distance between the inner wall of the inflated shaped balloon. The toroidal-shaped balloon can be slid off of the tube 12 and an inflation tube 14 as depicted in FIG. 7 can be inserted through the wall of the balloon and sealed. Any number of conventional ways of sealing the inflation tube to the balloon can be employed such as heat welding, ultrasonic welding or adhesives. In a preferred embodiment, the inflation tube 14 is inserted through the sealed region 6, however the inflation tube can be inserted anywhere on the balloon. In one embodiment, as depicted in FIG. 11, the inflation tube 14 in inserted and sealed along the outer diameter 3 of the inflated toroidal-shaped balloon 1. The inflation tube may also be inserted through the inflation hole in the side of the tube prior to inflating and sealing the balloon into a toroidal shape. In this way, the inflation tube becomes encapsulated in the sealed region of the balloon as depicted in FIGS. 7, 14, and 15. A catheter 15 may be employed with the shaped balloon 1.

The composite film 8 of the present invention comprises a porous reinforcing layer and a continuous polymer layer 10, as depicted in FIGS. 2 to 4. In one embodiment, the porous reinforcing polymer layer 9 is a thin, strong porous membrane that can be made in sheet form. The porous reinforcing polymer can be selected from a group of polymers including but not limited to: olefin, PEEK, polyamide, polyurethane, polyester, polyethylene, and polytetrafluoroethylene.

The preferred porous reinforcing polymer of the present invention is an ePTFE membrane made in accordance with the teachings of U.S. Pat. No. 3,953,566 or U.S. Pat. No. 5,476,589. It is even more preferable that the porous reinforcing polymer is expanded polytetrafluoroethylene (ePTFE). These thin, strong, and membranes enable the balloon to achieve large diameters and sustain high inflation pressures. An anisotropic ePTFE membrane is highly oriented in the one direction. An ePTFE membrane with a matrix tensile value in one direction of greater than 690 megapascals is preferred, and greater than 960 megapascals is even more preferred, and greater than 1,200 megapascals is most preferred. The exceptionally high matrix tensile value of ePTFE membrane allows the composite material to withstand very high hoop stress in the inflated balloon configuration. In addition, the high matrix tensile value of the ePTFE membrane makes it possible for very thin layers to be used which reduces the deflated balloon profile. A small profile is necessary for the balloon to be able to be positioned in small arteries or veins or orifices. In order for balloons to be positioned in some areas of the body, the balloon catheter must be able to move through a small bend radius, and a thinner walled tube is typically much more supple and capable of bending in this manner without creasing or causing damage to the wall of the vessel.

The shaped balloon of the present invention is able to realize an inflated outer diameter of greater than 10 mm at an inflation pressure of about 10 atmospheres and maintain the shape profile. More preferred, the shaped balloon of the present invention is able to realize an inflated diameter of about or greater than 20 mm, and an axial length of about 5 mm at an inflation pressure of 10 atmospheres and maintain the shape profile. In another preferred embodiment, the shaped balloon of the present invention is able to realize an inflated toroidal shape with an inflated diameter of at least 10 mm at an inflation pressure of 3 atmospheres or greater and maintain the shape profile and allow for partial flow through the vessel.

In another embodiment, the ePTFE membrane is mechanically homogeneous. The mechanically balanced ePTFE membrane can increase the maximum hoop stress that the composite film made therefrom can withstand. One example of such a membrane is found in U.S. patent application Ser. No. 11/334,243.

The continuous polymer layer 10 of the present invention is coated onto at least one side of the porous reinforcing polymer 9 as depicted in FIGS. 2 to 4. The continuous polymer layer is preferably an elastomer, such as but not limited to, aromatic and aliphatic polyurethanes including copolymers, styrene block copolymers, silicones, preferably thermoplastic silicones, fluoro-silicones, fluoroelastomer, THV, and latex. In one embodiment of the present invention, the continuous polymer layer 10 is coated onto only one side of the porous reinforcing polymer, as shown in FIG. 3. As depicted in FIG. 2, the continuous polymer layer 10 is coated onto both sides of the porous reinforcing polymer 9. In a preferred embodiment as depicted in FIG. 4, the continuous polymer layer 10 is imbibed into the porous reinforcing polymer 9 forming an imbibed polymer 11 which fills the pores of the porous reinforcing polymer 9.

The continuous polymer layer can be applied to the porous reinforcing polymer through any number of conventional methods including but not limited to, lamination, transfer roll coating, wire-wound bar coating, reverse roll coating, and solution coating or solution imbibing. In a preferred embodiment, the continuous polymer layer is solution imbibed into the porous reinforcing polymer as depicted in FIG. 4. In this embodiment, the continuous polymer layer polymer is dissolved in a suitable solvent and coated onto and throughout the porous reinforcing polymer using a wire-wound rod process. The coated porous reinforcing polymer is then passed through a solvent oven and the solvent is removed leaving a continuous polymer layer coated onto and throughout the porous reinforcing polymer. In some cases, such as when silicone is used as the continuous polymer layer, the coated porous reinforcing polymer may not require the removal of solvent. In another embodiment, the continuous polymer layer is coated onto at least one side of the porous reinforcing polymer and subsequently cured. In one such example, an ultraviolet light (UV) curable urethane may be used as the continuous polymer layer and coated onto the porous reinforcing polymer. The composite film comprising the porous reinforcing polymer and the UV curable urethane continuous polymer layer can then be wrapped around the tube, formed into a toroidal shape and then exposed to UV light and cured.

Figure 16:
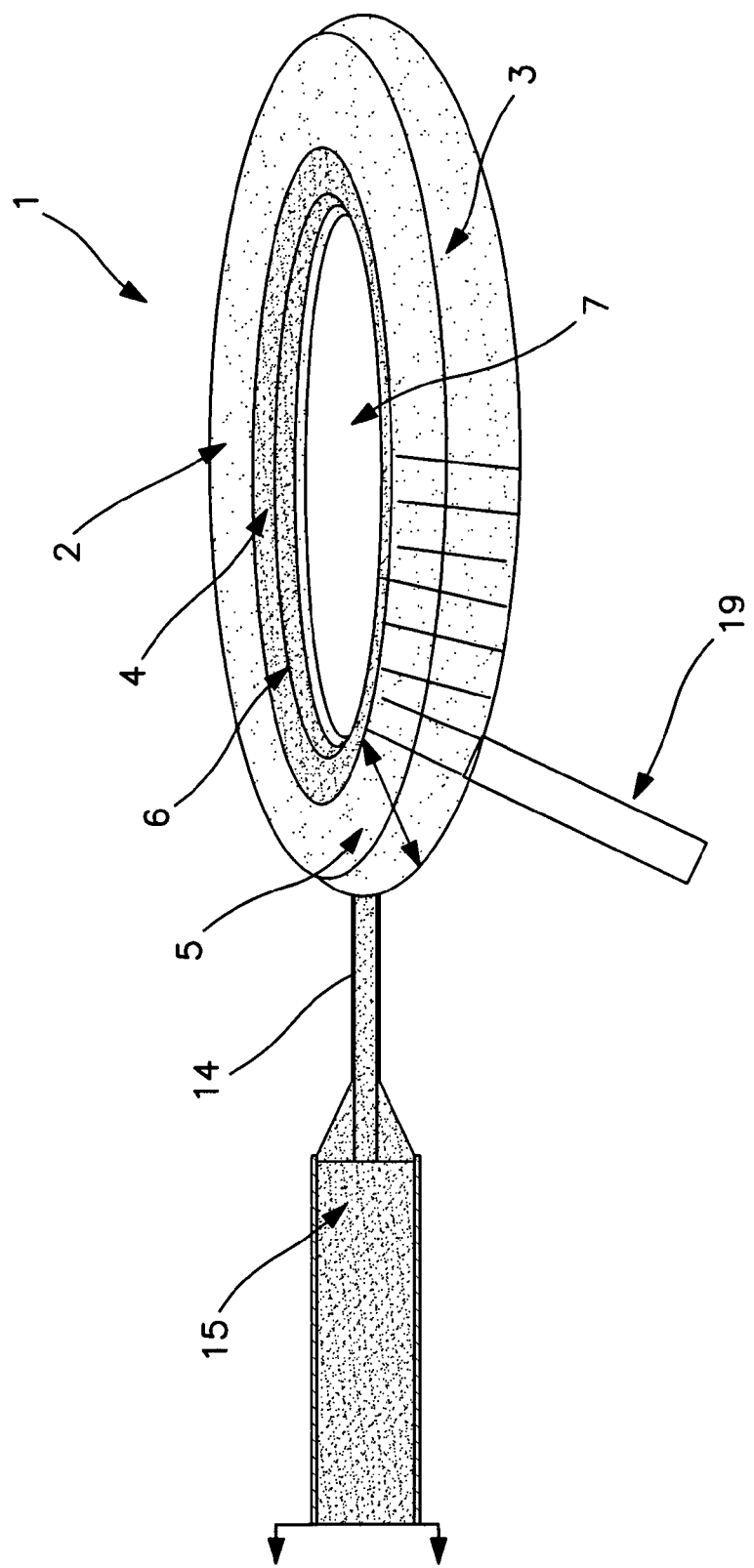
FIG. 16 shows a schematic representation of an inflated toroidal-shaped balloon catheter with an inflation tube connected along the outer diameter of the inflated balloon and an outer configuration layer wrapped onto the inflated balloon.

The balloons of the present invention can be further reinforced with the addition of an outer configuration layer 19 as depicted in FIG. 16. The outer configuration layer can be a composite film 8, or a porous reinforcing polymer 9 as described in the present invention, and can be attached to the balloon through any number of conventional methods including but not limited to, adhesion, heat sealing, UV curing, and ultrasonic welding. In a preferred embodiment, the outer configuration layer is made with ePTFE membrane; one such membrane is taught in U.S. patent application Ser. No. 11/334,243.

Figure 8:
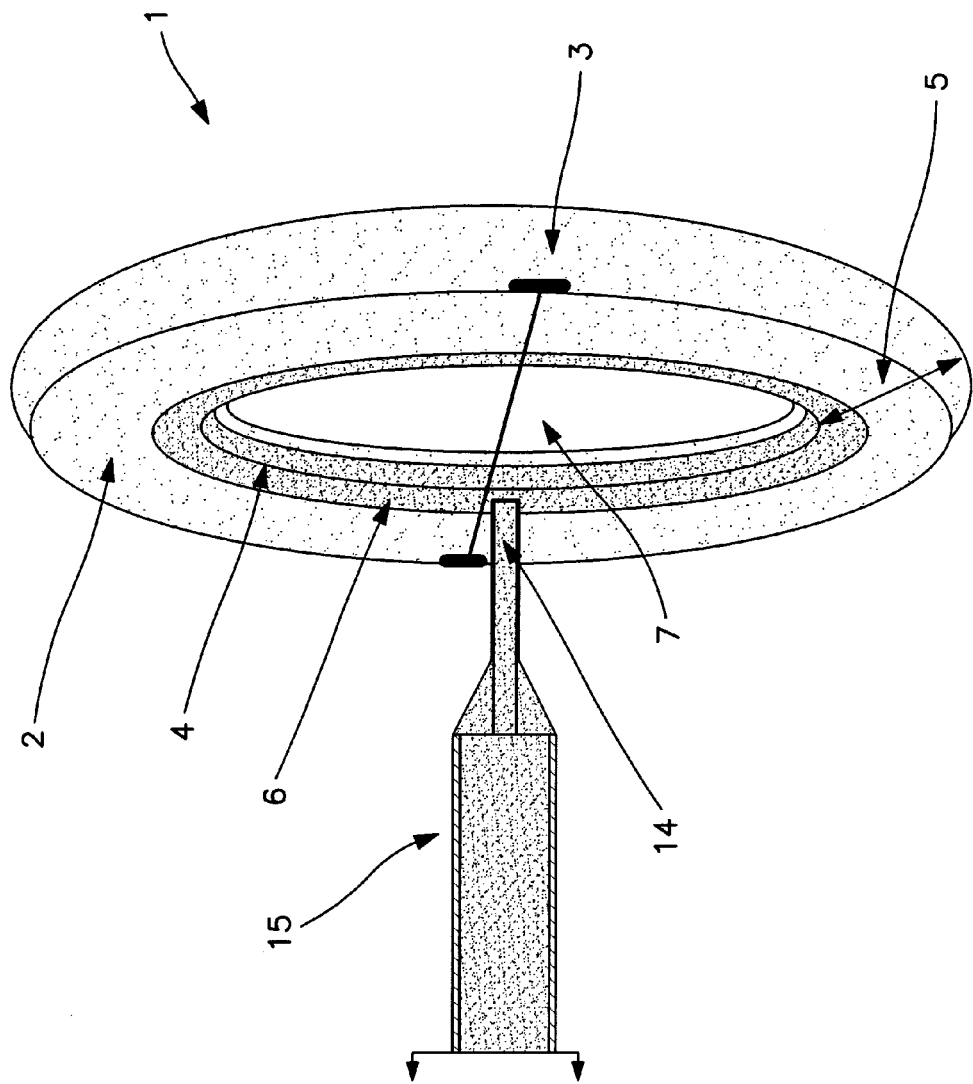
FIG. 8 shows a schematic representation of an inflated toroidal-shaped balloon catheter having a high outer diameter to inflated balloon diameter ratio.

The toroidal-shaped balloon of the present invention can withstand high inflation pressures for the outer diameter achieved. This is because the outer diameter 3 is larger than the inflated balloon diameter 5, as shown in FIG. 1. The hoop stress is proportional to the product of the pressure of inflation and the balloon diameter 3, divided by the wall thickness of the inflated balloon. For a given inflation pressure, the toroidal-shaped balloons of the present invention can be constructed to have much larger outer diameters 3 than a conventional tubular balloon made of the same material. In a preferred embodiment the outer diameter 3 of the balloon is greater than 1.5 times the inflated balloon diameter 5 as depicted in FIG. 7. In a more preferred embodiment, the outer diameter 3 is greater than 2.0 times the inflated balloon diameter, and in the most preferred embodiment, the outer diameter 3 is greater than 3.0 times the inflated balloon diameter as depicted in FIG. 8.

The maximum hoop stress of the inflated balloons of the present invention are much greater than those of conventional angioplasty balloons. The porous reinforcing polymer greatly increases the maximum hoop stress and allows the balloon to maintain a shape in an inflated state under high inflation pressure. In a preferred embodiment, high matrix tensile strength ePTFE membrane is used as the porous reinforcing polymer and an inflated balloon with an outer diameter 3 of greater than 6 mm is made to withstand a hoop stress of greater than 400 megapascals. In a more preferred embodiment the balloon is made to withstand a hoop stress of greater than 600 megapascals.

Figure 13:
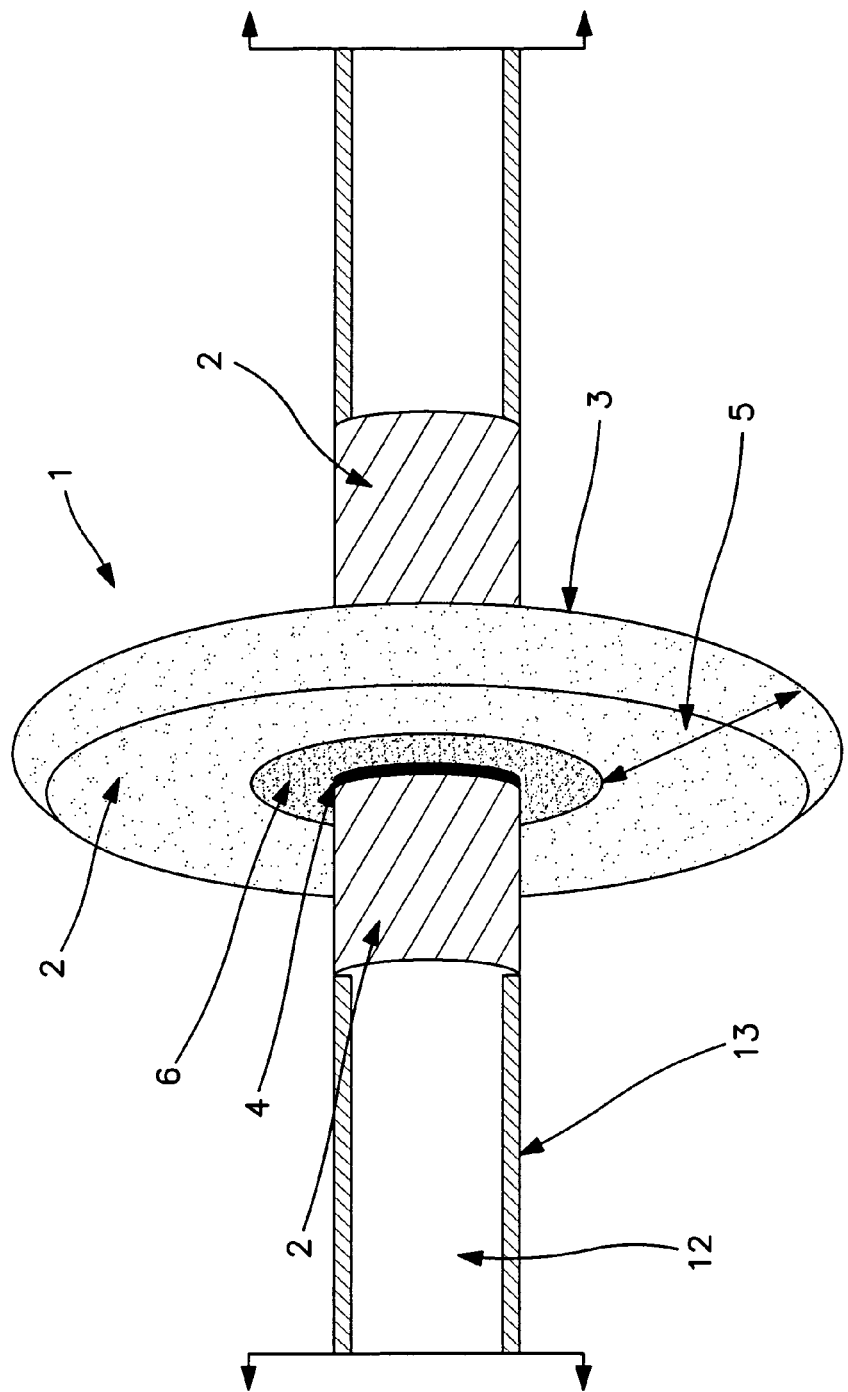
FIG. 13 shows a schematic representation of an inflated toroidal-shaped balloon with an additional length of unsealed wrapped layers on the tube.

The balloons of the present invention can be attached to a catheter through any number of conventional means. In a preferred embodiment as depicted in FIGS. 13 and 14, excess length of the wrapped layers 2 are used to seal the balloon 1 to the catheter 15. Additional wraps of composite film or porous reinforcing polymer can be used to further increase the bond to the catheter. In another embodiment, two toroidal-shaped balloons 1 are formed with excess length of wrapped layers 2 connecting the two balloons as depicted in FIG. 15. An inflation tube 14 is present on each shaped balloon 1. The sealed region 6 of the balloons is positioned to allow the inner diameter 4 of the balloons to be positioned around the tube 14. A release layer is present for ease of removal.

Figure 9:
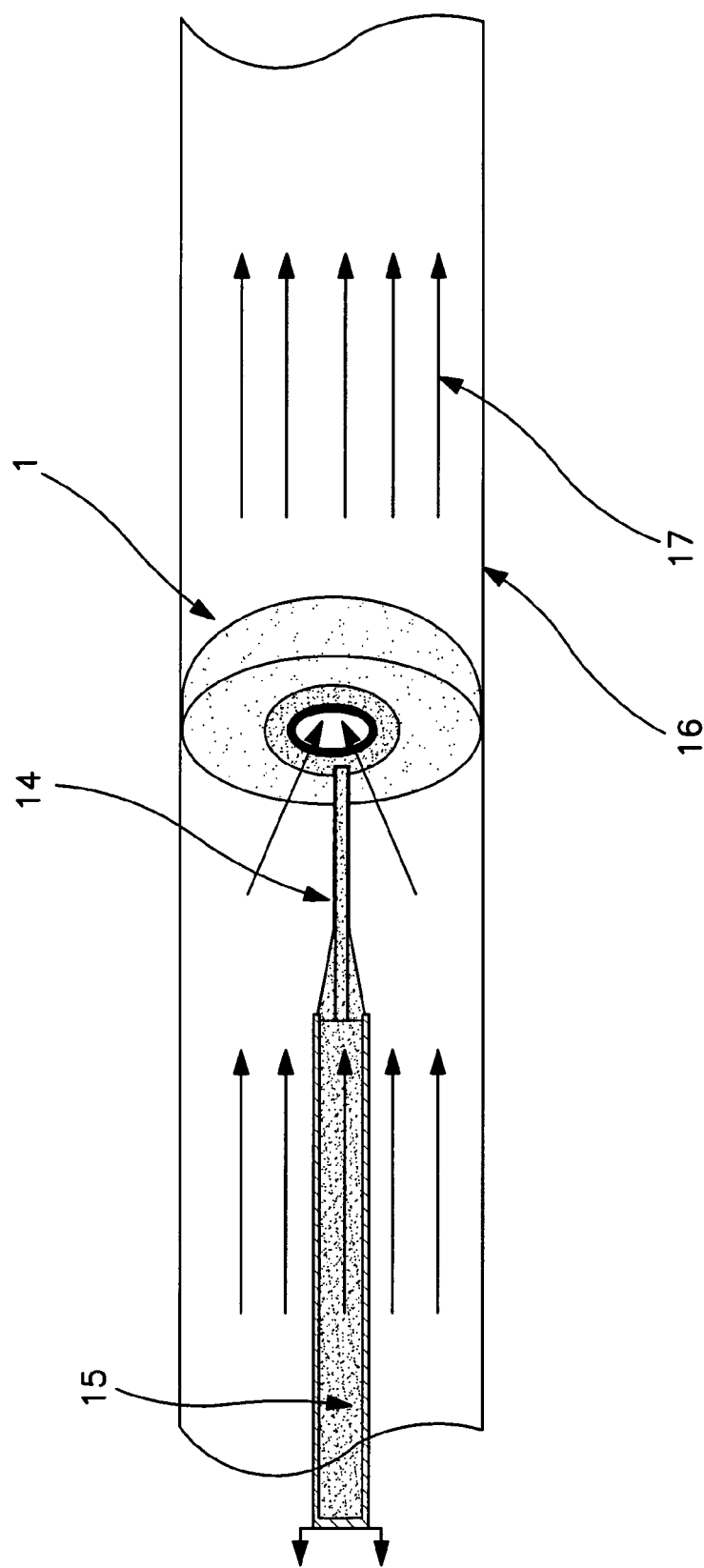
FIG. 9 shows a schematic representation of an inflated toroidal-shaped balloon catheter deployed in a vessel and perfusion flow.

The balloons of the present invention, when attached to a catheter, are capable for use in various surgical procedures including but not limited to angioplasty, stent or graft delivery and distention, and temporary brachytherapy as well as intestinal procedures and embolic protection. The toroidal-shaped balloons of the present invention are particularly useful in procedures requiring a large diameter elastomeric balloon catheter. In a preferred embodiment, the balloon is made with an open region 7 that allows for flow 17 through the inflated toroidal-shaped balloon 1, deployed in a conduit or vessel 16 as depicted in FIG. 9. When the toroidal balloon of the present invention is attached to a sheath or sleeve, bodily fluids are able to pass through the open region 7 of the balloon and channel through the sleeve. This type of a device is especially useful for large body cavities and conduits such as intestines.

Figure 12:
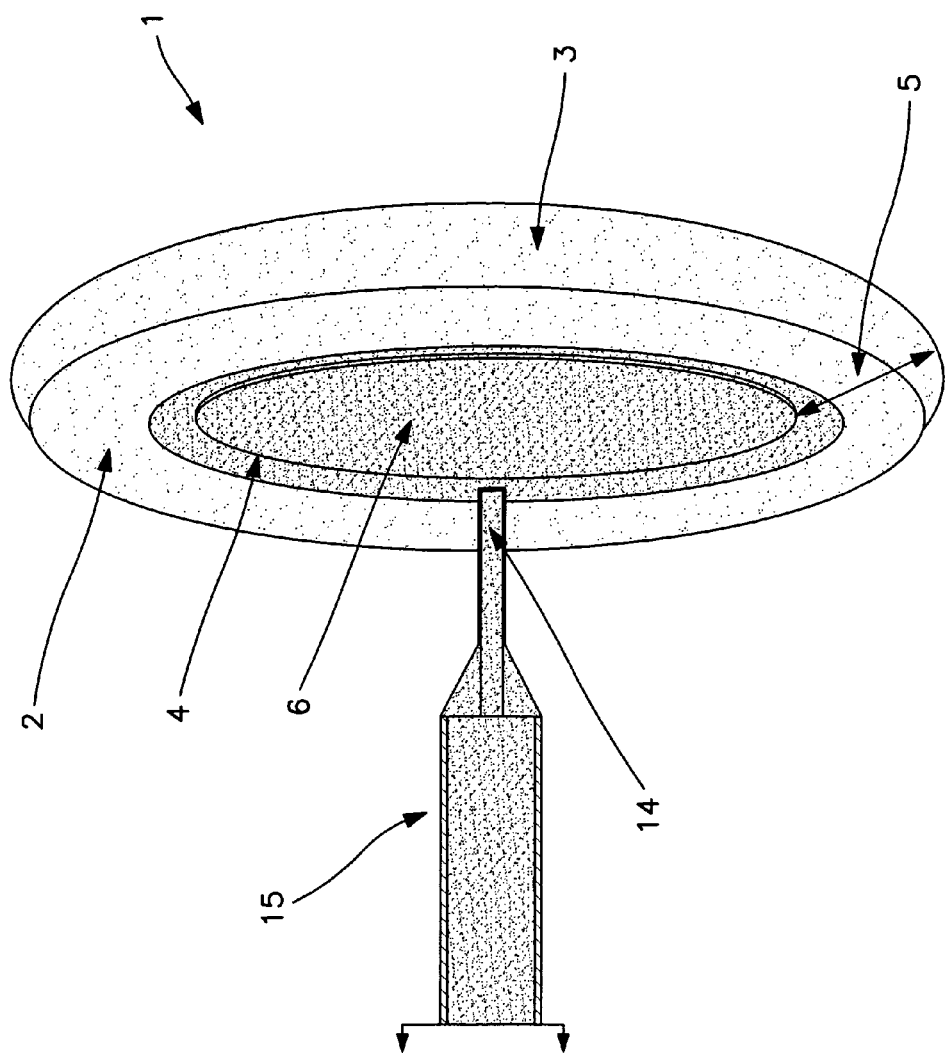
FIG. 12 shows a schematic representation of an inflated toroidal-shaped balloon catheter having a high outer diameter to inflated balloon diameter ratio and a sealed region within the inner diameter of the inflated balloon.

In yet another embodiment as depicted in FIG. 12, the open region is eliminated and the region within the inner diameter 4 of the inflated toroidal-shaped balloon 1 is completely sealed 6 to prevent any flow through the balloon. The open region can be sealed using the excess wrapped material not initially sealed to form the toroidal-shaped balloon, or a separate piece of material can be secured along the face of the balloon, or an outer configuration layer of material may be used to encapsulate the entire inflated balloon.

Figure 10:
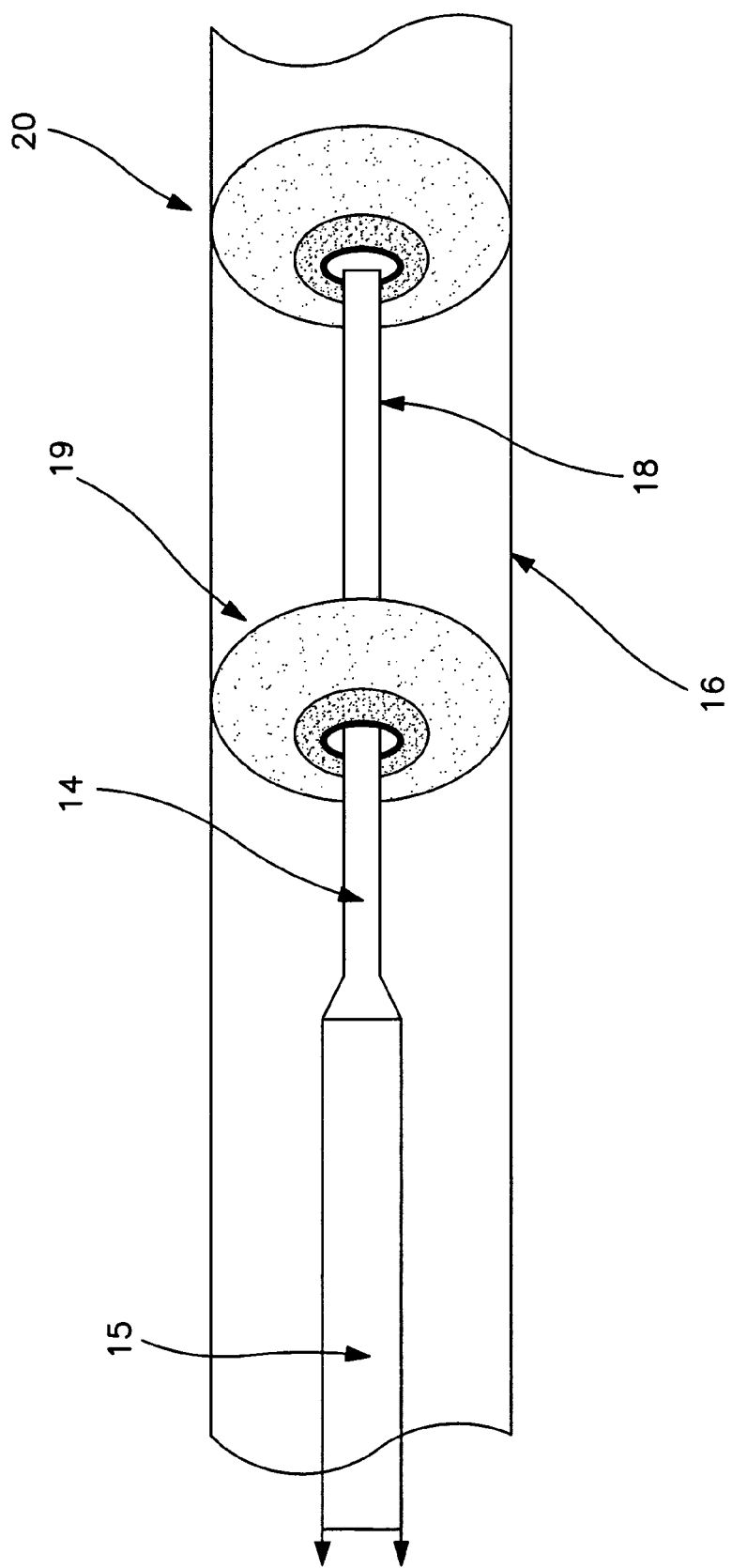
FIG. 10 shows a schematic representation of two inflated toroidal-shaped balloons attached to a catheter with a treatment element secured between the centers of the two balloons.

In yet another embodiment of the present invention as depicted in FIG. 10, a treatment element 18 is secured between a proximal inflated toroidal-shaped balloon 19 and a distal inflated toroidal-shaped balloon 20, wherein the treatment element is located approximately in the center of the vessel 16. In this embodiment the treatment element may be positioned between the two inflated balloons through the catheter. The ability to secure a treatment element in the center of vessel or orifice is especially valuable when radioactive materials are used as the treatment element such as temporary brachytherapy procedures.

In another embodiment of the present invention, the open region 7 can be made to close upon inflation of the balloon. This would allow the balloon to be positioned in a vessel and then decrease flow upon inflation. In a preferred embodiment, the balloon is used to control the flow rate through a vessel through the use of inflation pressure. In another embodiment, the balloon with a closing open region 7 during inflation is used to secure devices or tissue for placement, delivery into or removal from the body.

In another embodiment of the present invention, a bioresorbable polymer is used as the porous reinforcing polymer in the construction of the balloon. Bioresorbable polymers can also be used as the continuous polymer layer and enable placement of a porous reinforcing polymer after being absorbed by the body. This use of the present invention may be of particular value in intestinal or abdominal hernia applications, or aneurysm applications. In yet another embodiment of the present invention, a bioresorbable polymer is used in the construction of the composite film and is used as an inflation fluid to deploy the balloon. This embodiment may be useful in trauma wound closure applications.

In another embodiment, the balloon of the present invention can be made to detach from the catheter after location in the body, and inflation. In this embodiment it is preferred that the composite film be made to be self sealing such that the balloon stays inflated after removal of the inflation tube. In another embodiment, the inflation tube can be sealed and the catheter can be made to detach from the inflation tube after locating and inflating the balloon. The present invention may be further used to control flow through a vessel comprising the steps of positioning the toroidal-shaped balloon in a desired location in a vessel; and then inflating the balloon to a desired pressure to modulate the inner diameter of the balloon, thereby either increasing or reducing the open area and modulating flow through the vessel.

While particular embodiments of the present invention have been illustrated and described herein, the present invention should not be limited to such illustrations and descriptions. It should be apparent that changes and modifications may be incorporated and embodied as part of the present invention within the scope of the following claims. The following examples are further offered to illustrate the present invention.

EXAMPLES

Example 1

Composite Film Preparation

A composite film was made by using a wire-wound rod coating process whereby a solution of Tecothane TT-1085A polyurethane and tetrahydrofuran (THF) was coated onto an ePTFE membrane. The ePTFE membrane used to make the composite film was made in accordance with general the teaching in U.S. Pat. No. 5,476,589. Specifically, the ePTFE membrane was longitudinally expanded to a ratio of 55 to 1 and transversely expanded approximately 2.25 to 1, to produce a thin strong membrane with an mass of approximately 3.5 g/m$^2$ and a thickness of approximately 6.5 micrometers. A 3% to 8% by weight solution of Tecothane TT-1085A polyurethane in THF was coated onto the ePTFE membrane to produce a composite film with approximately equal amounts of Tecothane TT-1085A polyurethane on either side and throughout the ePTFE membrane and a total polymer weight application of approximately 40% to 60% of the total final composite film weight.

Example 2

Toroidal-Shaped Balloon

A 30.5 cm long, 4.8 mm outer wall diameter stainless steel tube was cigarette wrapped with two layers of an expanded PTFE membrane and EFEP (ethylene-perfluoroethylenepropene) fluoroplastic composite with the EFEP layer facing the stainless steel tube. This ePTFE/EFEP composite film was wrapped around the tube to provide a low friction slip layer. The ePTFE membrane/EFEP composite was approximately 50 um thick. The wrapped tube was then placed into a convection oven set to 250° C. for 30 minutes. An approximately 1.5 mm diameter hole was drilled through one side of a hollow stainless steel tube, approximately centered along the length.

A first pass with 2.5 cm wide composite film as described in Example 1 was helically wrapped around the center 15 cm long section of stainless steel tube at approximately 10 degrees from the longitudinal axis of the tube. The second pass of 2.5 cm wide composite film was then wrapped in the opposite direction at the same wrap angle over the same center portion length of the stainless steel tube. This process of wrapping in alternating directions was repeated until six passes were wrapped onto the tube.

The 2.5 cm wide composite film was then wrapped around the circumference of the tube, or at an angle of approximately 90 degrees from the longitudinal axis of the tube, four times centered on the tube with a 2.54 cm wide space between the edges of the wrap. The two circumferentially wrapped composite film sections were centered on the tube and over the hole previously drilled in the tube. The circumferentially wrapped sections of composite film were trimmed along the outside edges to approximately 9.5 mm wide, and the excess composite film wrap was discarded.

The wrapped tube was then passed over a hot box Balloon Development Station #210-A) (Beahm Designs, Inc, Campbell, Calif.), set to 135° C. The length of the composite film wrap was passed over the hot box in approximately 10 seconds.

One end of the hollow stainless steel tube was sealed closed with a stopper and the other was connected to a compressed air line, and the pressure was slowly increased to approximately 0.68 atmospheres.

The center section of the wrapped layers of composite film increased in diameter as the pressure increased. Heated pinchers were preheated to 170° C. and then slid snugly over the circumferentially wrapped sections and slid toward the center and pinched together and held for approximately 10 seconds to create a seal region along the inner diameter of the balloon.

The sealed shaped balloon was then slid off the tube and an inflation tube was inserted into the inner diameter of the balloon and sealed with a soldering iron. This process produced an approximately 12 mm outer diameter donut shaped balloon.

Example 3

Test Methods

Tensile Break Load Measurements and Matrix Tensile Strength Calculations Tensile break load was measured using an INSTRON 1122 tensile test machine equipped with flat-faced grips and a 0.445 kN load cell. The gauge length was 5.08 cm and the cross-head speed was 50.8 cm/min. The sample dimensions were 2.54 cm by 15.24 cm. For longitudinal MTS measurements, the larger dimension of the sample was oriented in the machine, also known as the down web direction. For the transverse MTS measurements, the larger dimension of the sample was oriented perpendicular to the machine direction, also known as the cross web direction. Each sample was weighed using a Mettler Toledo Scale Model AG204, then the thickness of the samples was taken using the Kafer FZ1000/30 thickness gauge. The samples were then tested individually on the tensile tester. Three different sections of each sample were measured. The average of the three maximum load (i.e., the peak force) measurements was used. The longitudinal and transverse MTS were calculated using the following equation:

MTS=(maximum load/cross-section area)*(bulk density of PTFE)/density of the porous membrane), wherein the bulk density of PTFE is taken to be 2.2 g/cc.

The invention claimed is:

1. An inflatable balloon for medical use comprising at least two helically wrapped layers formed into a wrapped balloon with a sealed region at least partially radially surrounded by an inflatable region, and an inflation means; wherein the sealed region is formed from the wrapped layers, extends along a length in a radial dimension, does not inflate, and is adjacent to an opening traversing an open region passing through the balloon in an inflated state.

2. The balloon of claim 1 wherein the inflatable region conforms to seal vessels or span a void within a tissue.

3. The balloon of claim 1 wherein the balloon is bioresorbable.

4. The balloon of claim 1 further comprising a bioresorbable media used to reach an inflated state.

5. The balloon of claim 1 wherein the balloon inflates to a toroidal shape.

6. The balloon of claim 5 wherein the inflatable balloon comprises an outer diameter that is greater than 1.5 times a diameter of the inflatable region.

7. The balloon of claim 5 wherein the inflatable balloon comprises an outer diameter that is greater than 2.0 times a diameter of the inflatable region.

8. The balloon of claim 5 wherein the inflatable region comprises an outer diameter that is greater than 3.0 times a diameter of the inflatable region.

9. The balloon of claim 5 wherein the inflatable region conforms to seal wound openings.

10. The balloon of claim 5 wherein at least one of the helically wrapped layers are oriented at an angle less than or equal to about 55 degrees.

11. The balloon of claim 1 wherein the helically wrapped layers are anisotropic.

12. The balloon of claim 5 further comprising a sleeve with an open channel.

13. The balloon of claim 12 wherein the open region closes upon inflation.

14. The balloon of claim 1 wherein the balloon is a catheter balloon for opening obstructions in vessels and permits through flow of blood.

15. The balloon of claim 1 wherein the balloon exhibits concentric deflation.

16. The balloon of claim 1 wherein the balloon is detachable from the inflation means.

17. The balloon of claim 1 wherein the balloon is comprised of a self-sealing material.

18. The balloon of claim 1 wherein at least one of the helically wrapped layers comprises a porous reinforcing polymer.

19. The balloon of claim 18 wherein the porous reinforcing polymer comprises a fibrous reinforcement.

20. The balloon of claim 18 wherein the porous reinforcing polymer is a PEEK.

21. The balloon of claim 18 wherein the porous reinforcing polymer is a polyamide.

22. The balloon of claim 18 wherein the porous reinforcing polymer is a polyurethane.

23. The balloon of claim 18 wherein the porous reinforcing polymer is a polyester.

24. The balloon of claim 18 wherein the porous reinforcing polymer is a fluoropolymer.

25. The balloon of claim 18 wherein the porous reinforcing polymer is an olefin.

26. The balloon of claim 18 wherein the porous reinforcing polymer is bioresorbable.

27. The balloon of claim 18 wherein the porous reinforcing polymer is expanded PTFE.

28. The balloon of claim 27 wherein the expanded PTFE has a matrix tensile value in one direction of greater than 690 megapascals.

29. The balloon of claim 27 wherein the expanded PTFE has a matrix tensile value in one direction of greater than 960 megapascals.

30. The balloon of claim 27 wherein the expanded PTFE has a matrix tensile value in one direction of greater than 1,200 megapascals.

31. The balloon of claim 27 wherein the maximum hoop stress of the helically wrapped layers is greater than 400 megapascals.

32. The balloon of claim 27 wherein the maximum hoop stress of the helically wrapped layers is greater than 600 megapascals.

33. The balloon of claim 18 wherein the wrapped layers comprise a porous reinforcing polymer and a continuous polymer layer.

34. The balloon of claim 33 wherein the continuous polymer layer is imbibed throughout the porous reinforcing polymer.

35. The balloon of claim 33 wherein the continuous polymer layer forms a surface coating layer on at least one side of the porous reinforcing polymer.

36. The balloon of claim 33 where the continuous polymer layer is comprised of a fluoropolymer.

37. The balloon of claim 33 where the continuous polymer layer is an elastomer.

38. The balloon of claim 33 wherein the continuous polymer layer is a urethane.

39. The balloon of claim 33 wherein the continuous polymer layer is a silicone.

40. The balloon of claim 33 wherein the continuous polymer layer is a fluoro-elastomer.

41. The balloon of claim 33 wherein the continuous polymer layer is bioresorbable.

42. An inflatable balloon for medical use comprising at least two helically wrapped layers formed into at least two wrapped balloons each with a sealed region and at least partially radially surrounded by an inflatable region, a treatment element and an inflation means; wherein the sealed region is formed from the wrapped layers, extends along a length in a radial dimension, does not inflate, and is adjacent to an open region passing through the balloon in an inflated state.

43. The balloon of claim 42, wherein treatment element is radioactive.

44. The balloon of claim 42, wherein treatment element is a therapeutic agent.

45. A method of controlling the flow through a vessel comprising the steps of positioning a toroidal-shaped balloon in a desired location in a vessel, wherein said toroidal-shaped balloon comprises at least two helically wrapped layers formed into the toroidal-shaped balloon with a sealed region formed from the wrapped layers and at an inner diameter of the balloon and extending along a length in a radial dimension, wherein the sealed region does not inflate and is at least partially radially surrounded by an inflatable region; and inflating the balloon to a desired pressure thereby reducing an open area and reducing the flow through the vessel.

46. The method of claim 45 wherein the vessel is a blood vessel.

47. The method of claim 45 wherein the flow is blood flow.

48. A method of controlling the flow through a vessel comprising the steps of: positioning a toroidal-shaped balloon in a desired location in a vessel, wherein said toroidal-shaped balloon comprises at least two helically wrapped layers formed into the toroidal-shaped balloon with a sealed region formed from the wrapped layers and at an inner diameter of the balloon and extending along a length in a radial dimension, wherein the sealed region does not inflate and is at least partially radially surrounded by an inflatable region; and inflating the balloon to a desired pressure thereby increasing a diameter of the vessel and increasing an open area and increasing flow through the vessel.

49. The method of claim 48 wherein the vessel is a blood vessel.

50. The method of claim 48 wherein the flow is blood flow.

* * * * *